United States Patent [19]

Qurnell et al.

[11] 4,383,394
[45] May 17, 1983

[54] SAMPLE CUTTING DEVICE FOR IRRADIATED COMPONENTS

[75] Inventors: Frank D. Qurnell, San Jose; Arthur V. Peloquin, Danville, both of Calif.

[73] Assignee: General Electric Company, San Jose, Calif.

[21] Appl. No.: 220,826

[22] Filed: Dec. 29, 1980

[51] Int. Cl.³ .................. B23D 45/02; B23D 47/02
[52] U.S. Cl. ..................................... 51/241 S; 51/327; 83/34; 83/54; 83/745; 83/486.1; 83/919; 83/925 R
[58] Field of Search .................. 83/34, 54, 167, 745, 83/486.1, 919, 925 R, 22; 125/13, 14; 51/35, 37, 241 S, 327

[56] References Cited

U.S. PATENT DOCUMENTS

| 1,946,390 | 2/1934 | Christiansen | 83/745 |
| 3,396,713 | 8/1968 | Schuman | 125/14 |
| 3,672,247 | 6/1972 | Cherel | 83/925 R |
| 4,000,391 | 12/1976 | Yeo | 83/925 R |
| 4,318,391 | 3/1982 | Wachs | 125/14 |

Primary Examiner—James M. Meister
Attorney, Agent, or Firm—Ivor J. James, Jr.; Samuel E. Turner; Raymond G. Simkins

[57] ABSTRACT

A remotely operable device for cutting sample pieces from the walls of an irradiated component while the component is submerged in a pool of water to shield the operator from radiation.

7 Claims, 3 Drawing Figures

SAMPLE CUTTING DEVICE FOR IRRADIATED COMPONENTS

BACKGROUND

In known types of nuclear power reactors, for example as used in the Dresden Nuclear Power Station near Chicago, Illinois, the reactor core comprises a plurality of spaced fuel assemblies arranged in an array capable of self-sustained nuclear fission reaction. The core is contained in a pressure vessel wherein it is submerged in a working fluid, such as light water, which serves both as coolant and as a neutron moderator. Each fuel assembly comprises a removable tubular flow channel, typically of approximately square cross section, and formed for example of zirconium alloy, surrounding an array of elongated, cladded fuel elements or rods containing suitable fuel material, such as uranium or plutonium oxide, supported between upper and lower tie plates. A typical fuel assembly of this type is shown, for example, by B. A. Smith et al. in U.S. Pat. No. 3,431,170.

Additional information on nuclear power reactors may be found, for example, in "Nuclear Power Engineering", M. M. El-Wakil, McGraw-Hill Book Company, Inc., 1962.

The previously mentioned removable tubular flow channel which surrounds each fuel assembly is an example of a reactor component which potentially has a relatively long service life. Thus upon verification of its serviceability it can be reused on a replacement fuel assembly.

Apparatus which can be used at the reactor site for examining irradiated components such as flow channels to verify continued serviceability has been developed. For example, U.S. Pat. No. 4,143,251 describes a device for measuring the corrosion formation on the surface of such components while U.S. Pat. No. 4,197,652 describes a device for checking the dimensions of such components.

If such a component is found to be unserviceable, it is discarded. However, because it is radioactive, it cannot be scrapped in a conventional manner. The usual procedure is to place the rejected component in an underwater storage rack to await processing (such as compaction) for eventual permanent disposal.

With a view toward understanding the nature and causes of defects of such rejected components, so that improvements can be made, or for detailed examination of experimental or developmental components, it is found desirable to examine the portions of such components with laboratory equipment and techniques beyond those available as a practical matter at a reactor site.

The desire for laboratory examination of the defective portions raises several problems. Since only selected samples of the rejected component are needed for laboratory examination, transportation of the entire component is impractical and would merely transfer the problem of storage of the component from the reactor site to the laboratory. Thus the desired sample pieces should be cut from the component, such as a flow channel, at the reactor site and only these sample pieces transported to the laboratory.

Furthermore, while the reactor site is equipped to handle and store flow channels (and other components) as such, usually it is not well equipped to accommodate odd sized and shaped pieces that would result, for example, from cutting a fuel channel in two. Thus it is desirable to remove sample pieces from the rejected component without destruction of its structural integrity or change in its overall size and shape.

An object of this invention is remotely operable apparatus for removing sample pieces from an irradiated component.

A more specific object is apparatus which is remotely manipulatable for making cuts in the walls of an irradiated component whereby sample pieces can be removed without destroying the structural integrity of the component or changing its overall size and shape.

SUMMARY

These and other objects of the invention are achieved by a remotely operable sample cutting device which can be lowered into engagement with a selected portion of the walls of an irradiated component submerged in a pool of water to provide radiation shielding. The device includes a base assembly with a clamping arrangement for removably securing the device to the component. A guide assembly mounted on the base assembly carries a cutter head fitted with a cutting tool. The guide assembly includes remotely operable slides for moving the cutting tool into engagement with the wall of the component and for then moving the tool along the component to thereby make a cut in the wall. By reorienting the cutter head, successive cuts can be made at an angle to one another whereby a piece of the wall is cut free as a sample.

DRAWING

DESCRIPTION

The sample cutting device of the invention is described herein, by way of example, as adapted to cut sample pieces from the walls of an elongated tubular fuel assembly flow channel, such channel being formed of a relative thin sheet metal material such as a zirconium alloy.

Figure 1:
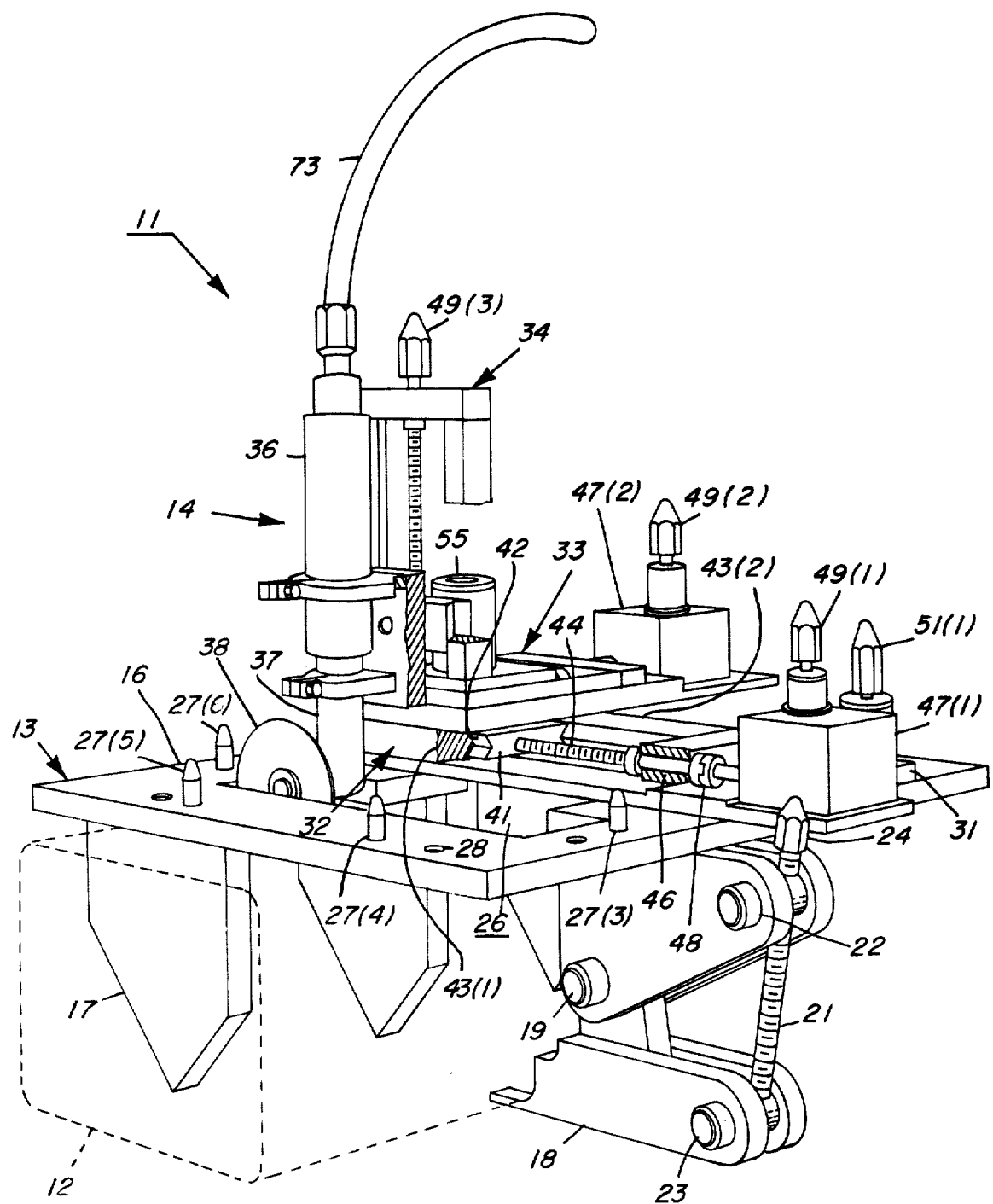
FIG. 1 is an isometric view of a sample cutting device in accordance with the invention.
Figure 2:
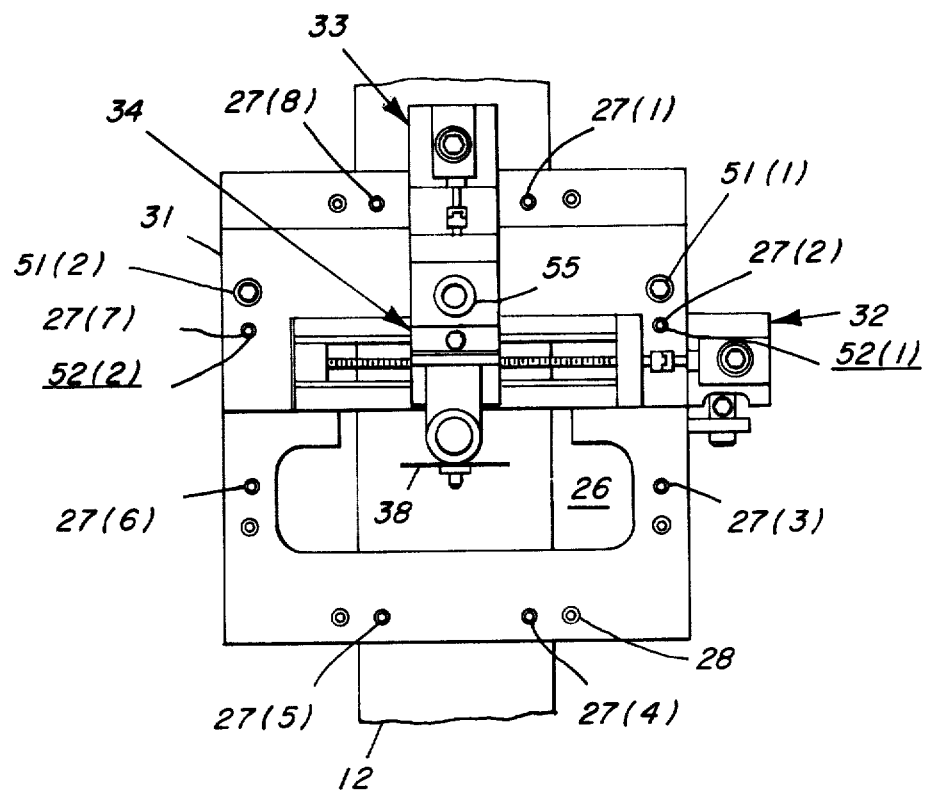
FIG. 2 is a plan view of the sample cutting device.

The sample cutting device 11, as illustrated in FIGS. 1 and 2 mounted on a flow channel 12 (shown in phantom view) consists of two main components, namely, a base assembly, 13 and a guide assembly 14 removably secured thereto.

The base assembly 13 includes a base plate 16 along one bottom side of which is attached two or more downwardly extending brackets 17 which locate the base assembly on the channel 12. Extending downward from the opposite bottom side of base plate 16 is a clamping device including a clamp jaw 18 pivoted on a pin 19. The clamp jaw 18 is movable in and out of engagement with the channel by a screw 21 threaded into a fixed pin 22 and journalled and captured in a pin 23 carried by the jaw 18. The screw 21 is fitted with a hexagonal head 24 by which it may be turned remotely from pool-side by use of a pole fitted with a drive socket 25 (FIG. 3) as discussed hereinafter. The brackets 17 and the clamping device including clamp jaw 18 thus form a clamping arrangement for removably securing the base assembly 13 to the channel 12.

Formed in the central portion of the base plate 16 is a relatively large cutout 26 to allow access of the cutting wheel to the wall of the channel 12 and for visual observation. Extending upward from the peripheral portion of the base plate 16 are four pairs of oppositely positioned alignment pins 27(1)–27(8) which serve to locate the guide assembly 14 in one of its four permitted positions on the base plate 16. Also formed in the peripheral portion of the base plate 16 are four pairs of oppositely positioned tapped holes 28 for receiving captive screws by which the guide assembly 14 is removably secured to the base plate 16.

The guide assembly 14 includes a base member 31 mounted on which is a long or main horizontal slide 32. Mounted on the main slide 32 is a short horizontal cross slide 33 which, in turn, carries a vertical slide 34. Mounted on the vertical slide 34 is a cutter head including a suitable motor 36 (such as a compressed air driven motor) coupled to an angle gear box 37 which is fitted with an arbor for removably receiving a suitable cutting wheel 38 (which may be, for example, a diamond faced cutting wheel of about 1 mm in thickness and in the order of 8 cm in diameter).

The main slide 32, the cross slide 33 and the vertical slide 34 may be similar in construction. The main slide 32, for example, includes a slide member 41 (to which is attached the cross slide 33) formed with V-shaped sides and fitted for sliding motion in V-shaped guide ways 42 formed in a pair of spaced guide members 43(1), 43(2). The slide member 41 is driven along the ways 42 by a lead screw 44 journalled in a bearing block 46 and engaging a threaded hole in the slide member 41.

Figure 3:
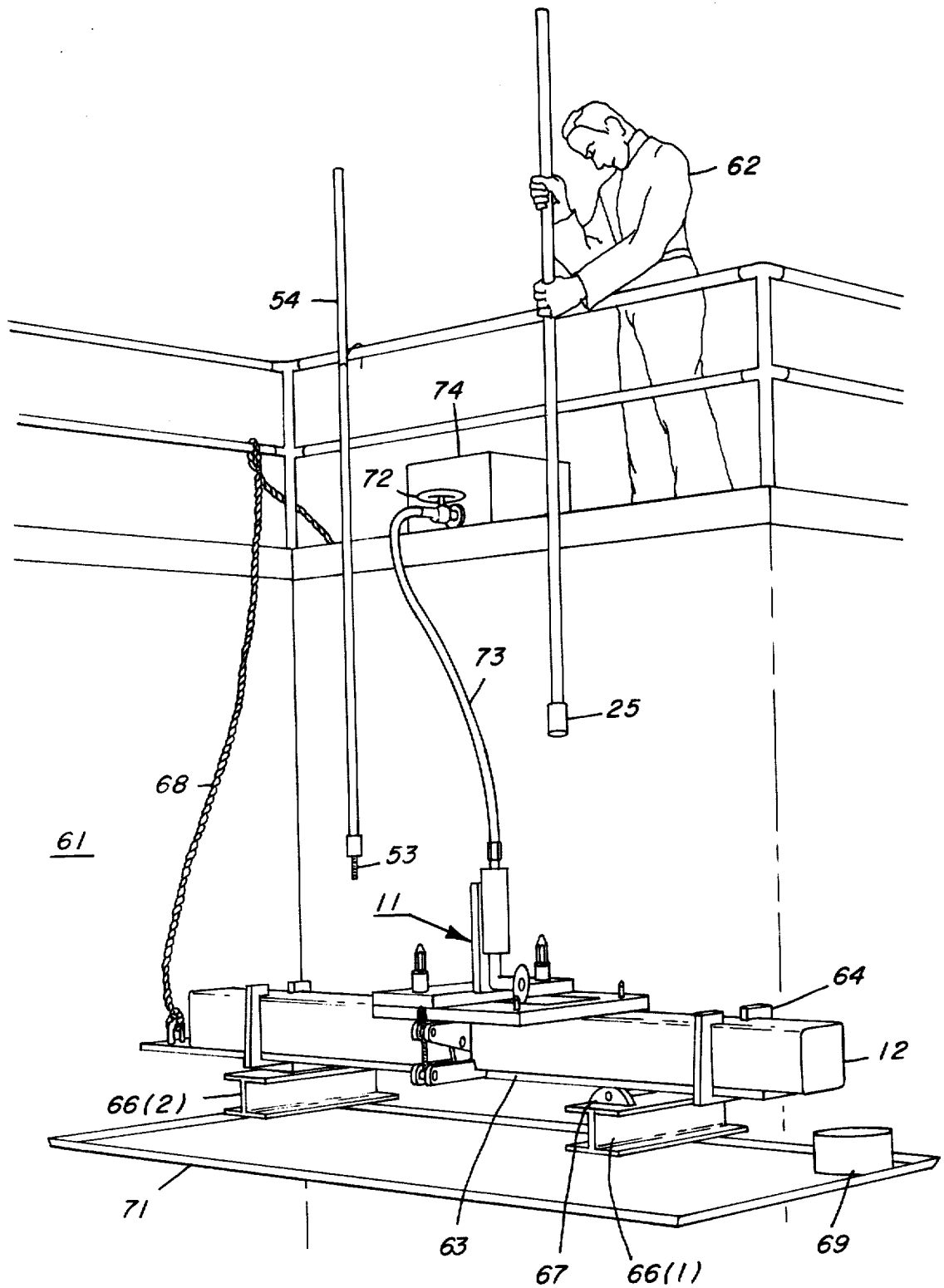
FIG. 3 is an illustration of the sample cutting device as used in a pool of shielding water to cut sample pieces from the walls of a fuel assembly channel.

To change the direction of drive, as is necessary for remote actuation from pool side, an angle gear box 47(1) is provided, the horizontal shaft of which is coupled by a coupling 48 to the lead screw 44 and the vertical shaft of which is fitted with a hexagonal nut 49(1) for receiving the previously mentioned pole-mounted drive socket 25 (FIG. 3).

A similar angle gear box 47(2) is coupled to the lead screw of the cross slide 33 and fitted with a drive nut 49(2) while a drive nut 49(3) is fitted directly to the lead screw of the vertical slide 34 since no drive direction change is needed there.

The guide assembly 14 is removably mounted on the base assembly 13 by a pair of captive screws 51(1) and 51(2) secured to base member 31 and engaging the previously mentioned tapped holes 28 in the base plate 16, the screws 51(1), 51(2) being fitted with hexagonal heads by which they can be actuated remotely. The base member 31 is also formed with a pair of holes 52(1) and 52(2) for receiving the previously mentioned alignment pins 27(1)–27(8) which project from the base plate 16 to define the four permitted positions of the guide assembly 14.

As illustrated in FIGS. 1 and 2, the guide assembly 14 is in a "rear" or first transverse cutting position as defined by alignment pins 27(2) and 27(7) with the cutting wheel 38 oriented for a transverse cut in the wall of the flow channel 12. To move the guide assembly 14 to one of its alternate positions the captive screws 51(1) and 51(2) are remotely loosened by use of the pole-mounted drive socket 25. A threaded stud 53, mounted at the end of a second pole 54 (FIG. 3) is then engaged with a threaded boss 55 secured, for convenience, to the slide member of the slide 33. Pole 54 can then be lifted to lift the guide assembly 14 out of engagement with alignment pins 27(2) and 27(7) and to move and/or turn the guide assembly 14 to another one of its positions including a second transverse cutting position defined by alignment pins 27(3) and 27(6), a first longitudinal cutting position defined by alignment pins 27(5) and 27(8) and a second longitudinal cutting position defined by alignment pins 27(1) and 27(4).

Use of the sample cutting device 11 is illustrated in FIG. 3. The fuel assembly channel, from which samples are to be cut, is supported in a horizontal position under a suitable depth of water in a pool 61 for shielding an operator 62 from radiation. For example, the channel 12 may be supported on a support plate 63 and removable secured thereto by suitable clamps 64.

The support plate 63 is, in turn, supported, for example, by a pair of spaced cantilever beams 66(1) and 66(2) and is secured to beam 66(1) by a hinge arrangement 67. A rope 68 attached to the other end of the support plate 63 thus allows the operator 62 to tip the support plate 63 and hence the channel 12 toward its vertical position. This allows the sample pieces, which fall to the inside of the channel 12 when they are cut free, to slide out of the channel 12 into a receptacle 69 from which they can be retrieved for shipment to the laboratory. A chip tray 71 suitably supported beneath the channel 12 is provided to catch the metal particles or chips resulting from the sample cutting operation.

Performance of the sample cutting operation is as follows: As mentioned hereinbefore the sample cutting device 11 can be manipulated from pool side by use of the pole 54 by engaging the threaded stud 53 at its end with the threaded boss 55 whereby the sample cutting device 11 is lowered onto the selected portion of the channel 12 (the vertical slide 34 being in its upper position so that the cutting wheel 38 does not engage the channel 12 at this time). The pole-mounted drive socket 25 is then used to turn screw 21 to bring the clamping jaw 18 into contact with the channel 12.

The pole-mounted socket 25 is also used, as previously discussed, for actuating the slides 32, 33 and 34 and for releasing and securing the captive screws 51(1) and 51(2). The short horizontal slide 33 can be used at this time for fine positioning of the cutting wheel 38.

When the cutting wheel 38 is in the desired position the motor 36 is turned on by opening a valve 72 in a supply line 73 between the motor 36 and a source of compressed air 74. The vertical slide 34 is now actuated to lower the cutting wheel 38 into cutting engagement with the channel 12 and the long horizontal slide 32 is then actuated to complete the first cut. Upon completion of a cut the vertical slide 34 is actuated to raise the cutting wheel 38 out of engagement with the channel 12.

Subsequent cuts can be made in a similar manner to complete the two pairs of cuts at right angles that are necessary to cut free a sample piece. For small sample pieces, spaced parallel cuts can be made by adjustment of the short horizontal slide 33. For larger sample pieces the guide assembly 14 is repositioned on the base assembly 13 as described hereinbefore and, in any event, the guide assembly 14 must be repositioned to make the second pair of parallel cuts at right angles to the first pair of parallel cuts.

What is claimed is:

1. A remotely operable device for cutting sample pieces from a radioactive component submerged in a pool of water to provide radiation shielding, said device comprising: a base assembly including a base plate for engaging said component; a clamp arrangement extending from said base plate for removably securing said device to said component; a cutter guide assembly mounted on said base plate; a cutter head including a cutting tool mounted on said guide assembly, said guide assembly including remotely operable guide means for moving said cutting tool into cutting engagement with said component and for moving said cutter head with respect to said component to thereby make a first cut; means for reorienting said cutter head with respect to said component for making successive cuts in said component at an angle to one another whereby a piece of said component is cut free as a sample; a plurality of pairs of alignment pins secured to said base plate to define a plurality of alternative positions of said guide assembly on said base assembly, each pair of said alignment pins being adapted to engage a pair of alignment pin receiving holes in said guide assembly.

2. The device of claim 1 including a pair of captive screws secured to said guide assembly and adapted to engage a respective pair of threaded holes in said base plate of said base assembly in each of said alternative positions of said guide assembly and means for remotely actuating said captive screws whereby said guide assembly is removably secured to said base plate.

3. A remotely operable device for cutting sample pieces from a radioactive component submerged in a pool of water to provide radiation shielding, said device comprising: a base assembly including a base plate for engaging said component; a clamp arrangement extending from said base plate for removably securing said device to said component; a cutter guide assembly mounted on said base plate; a cutter head including a cutting tool mounted on said guide assembly, said guide assembly including remotely operable guide means for moving said cutting tool into cutting engagement with said component and for moving said cutter head with respect to said component to thereby make a first cut; and means for reorienting said cutter head with respect to said component for making successive cuts in said component at an angle to one another whereby a piece of said component is cut free as a sample, said cutter head being mounted on the slide member of a vertical slide for moving said cutting tool toward and away from said component, said vertical slide being mounted on a horizontal slide arrangement for moving said cutting tool along said component, and said horizontal slide arrangement comprising a first horizontal slide mounted on the slide member of a second horizontal slide and at a right angle thereto, said vertical slide being mounted on the slide member of said first horizontal slide whereby said first horizontal slide provides fine positioning of said cutting tool with respect to said component and said second horizontal slide provides movement of said cutting tool along said component to make a cut therein.

4. The device of claim 3 wherein said slides are fitted with drive nuts for engagement with a pole-mounted drive socket for remote actuation of said slides.

5. An arrangement for cutting sample pieces from the walls of an irradiated open-ended nuclear fuel assembly flow channel, comprising: means for supporting said flow channel in a generally horizontal position in a pool of water for radiation shielding, a device for making selected cuts in a wall of said channel; remotely operable means for manipulating said device into a cutting position over a selected portion of said wall; means operable from pool-side for operating said device to make selected cuts in said channel at angles to one another whereby a sample piece of said channel is cut free to drop to the inside of said channel; means operable from pool-side for moving said channel toward a verical position whereby said sample piece slides out of the open end thereof; and a receptacle position below said open end of said channel for catching said sample piece.

6. The arrangement of claim 5 including a tray positioned beneath said flow channel to catch particles and chips resulting from said cutting operation.

7. A method for cutting sample pieces from the walls of an irradiated open-ended nuclear fuel assembly flow channel, comprising:
(1) supporting said channel in a generally horizontal position in a pool of water for radiation shielding;
(2) providing a device for making selected cuts in a wall of said channel;
(3) manipulating said device remotely from pool-side into a cutting position over a selected portion of said wall;
(4) operating said device remotely from pool-side to make selected cuts in said channel at angles to one another whereby a sample piece of said channel is cut free to drop to the inside of said channel;
(5) moving said channel toward a vertical position whereby said sample piece slides out of the open end of said channel; and
(6) positioning a receptacle adjacent said open end of said channel to catch said sample piece.

* * * * *